United States Patent [19]
Oster et al.

[11] Patent Number: 5,425,701
[45] Date of Patent: Jun. 20, 1995

[54] ORTHOPEDIC BRACE HAVING WIDTH ADJUSTING VAMP

[75] Inventors: Craig D. Oster, Oakdale, Minn.; David C. Byram, River Falls, Wis.; Dayton W. Hulst, St. Paul, Minn.

[73] Assignee: Minnesota Mining and Manufacturing Company, St. Paul, Minn.

[21] Appl. No.: 184,590

[22] Filed: Jan. 21, 1994

[51] Int. Cl.⁶ .................................................. D61F 5/00
[52] U.S. Cl. ........................................ 602/23; 602/27; 128/882
[58] Field of Search ............... 128/882; 602/65, 27, 602/23, 13, 12, 5

[56] References Cited

U.S. PATENT DOCUMENTS

| | | | |
|---|---|---|---|
| 398,892 | 3/1889 | Golden . | |
| 487,492 | 12/1892 | Pugsley . | |
| 2,410,560 | 11/1946 | Witte | 287/101 |
| 2,694,395 | 11/1954 | Brown | 128/38 |
| 3,732,861 | 5/1973 | Lehneis | 128/80 E |
| 3,805,773 | 4/1974 | Sichau | 128/80 E |
| 3,955,565 | 5/1976 | Johnson, Jr. | 128/89 R |
| 3,999,540 | 12/1976 | Freeman | 128/80 R |
| 4,057,056 | 11/1977 | Payton | 128/83.5 |
| 4,102,337 | 7/1978 | Golia | 128/80 E |
| 4,136,404 | 1/1979 | Lange | 2/22 |
| 4,166,460 | 9/1979 | Applegate | 128/80 H |
| 4,217,893 | 8/1980 | Payton | 128/89 R |
| 4,280,489 | 7/1981 | Johnson, Jr. | 128/80 H |
| 4,320,748 | 3/1982 | Racette et al. | 128/80 F |
| 4,323,058 | 4/1982 | Detty | 128/80 H |
| 4,378,793 | 4/1983 | Mauldin et al. | 128/80 H |
| 4,414,965 | 11/1983 | Mauldin et al. | 128/87 R |
| 4,446,856 | 5/1984 | Jordan | 128/80 R |
| 4,494,534 | 1/1985 | Hutson | 128/80 F |
| 4,505,269 | 3/1985 | Davies et al. | 128/87 R |
| 4,517,968 | 5/1985 | Greene et al. | 128/80 H |
| 4,554,912 | 11/1985 | Haberman | 128/80 E |
| 4,572,169 | 2/1986 | Mauldin et al. | 128/80 H |
| 4,628,945 | 12/1986 | Johnson, Jr. | 128/80 H |
| 4,693,239 | 9/1987 | Clover, Jr. | 128/80 F |
| 4,724,847 | 2/1988 | Nelson | 128/80 H |
| 4,727,863 | 3/1988 | Nelson | 128/80 H |
| 4,766,890 | 8/1988 | Hollrah | 128/89 R |
| 4,771,768 | 9/1988 | Crispin | 128/88 |
| 4,825,856 | 5/1989 | Nelson | 128/80 H |
| 4,844,094 | 7/1989 | Grim | 128/80 H |
| 4,919,118 | 4/1990 | Morris | 128/88 |
| 4,953,543 | 9/1990 | Grim et al. | 128/80 C |
| 4,962,760 | 10/1990 | Jones | 128/80 F |
| 4,964,402 | 10/1990 | Grim et al. | 128/80 H |
| 4,966,134 | 10/1990 | Brewer | 128/80 H |
| 4,974,583 | 12/1990 | Freitas | 128/80 R |
| 4,977,891 | 12/1990 | Grim | 128/80 H |
| 5,007,416 | 4/1991 | Burns et al. | 128/80 H |
| 5,014,691 | 5/1991 | Cueman et al. | 128/80 H |
| 5,020,523 | 6/1991 | Bodine | 128/80 R |
| 5,078,128 | 1/1992 | Grim et al. | 128/83.5 |
| 5,088,478 | 2/1992 | Grim | 602/27 |
| 5,088,481 | 2/1992 | Darby | 602/23 |
| 5,092,319 | 3/1992 | Grim | 602/27 |
| 5,092,321 | 3/1992 | Spademan | 602/27 |

(List continued on next page.)

OTHER PUBLICATIONS

Clircart Walking Brace brochure, 1989.

Primary Examiner—Robert A. Hafer
Assistant Examiner—Michael O'Neill
Attorney, Agent, or Firm—Gary L. Griswold; Walter N. Kirn; James D. Christoff

[57] ABSTRACT

An orthopedic brace to facilitate healing of injuries to the foot, ankle or portions of the leg above the ankle includes a boot having a lower edge section releasably connected to a sole. The width of the boot, as well as the distance between a pair of upright struts located along opposite sides of the boot, may be varied to complementally match the width of the patient's foot. The struts and a section of fastening straps are located between layers of foam pads of the boot to reduce the likelihood that the straps or struts will become ensnarled with other items. The sole has a mirror image configuration on either side of its longitudinal axis, and left and right insoles are provided so that a single boot may be used with either the left or right foot of the patient.

14 Claims, 4 Drawing Sheets

U.S. PATENT DOCUMENTS

| | | | |
|---|---|---|---|
| 5,125,400 | 6/1992 | Johnson, Jr. | 602/13 |
| 5,176,623 | 1/1993 | Stetman et al. | 602/27 |
| 5,183,036 | 2/1993 | Spademan | 602/10 |
| 5,199,941 | 4/1993 | Makinen | 602/27 |
| 5,209,722 | 5/1993 | Miklaus et al. | 602/27 |
| 5,217,431 | 6/1993 | Toronto et al. | 602/27 |
| 5,226,875 | 7/1993 | Johnson | 602/27 |
| 5,242,378 | 9/1993 | Baker | 602/23 |
| 5,250,021 | 10/1993 | Chang | 602/27 |
| 5,269,748 | 12/1993 | Lonardo | 602/27 |
| 5,329,705 | 7/1994 | Grim et al. | |
| 5,352,189 | 10/1994 | Schumann et al. | 602/23 |

ORTHOPEDIC BRACE HAVING WIDTH ADJUSTING VAMP

BACKGROUND OF THE INVENTION

1. Field of the Invention

The present invention relates to an orthopedic device, and more particularly to a brace for stabilizing the lower leg, ankle and foot after an injury in order to promote healing.

2. Background of the Invention

Injuries affecting the lower leg and foot are often treated by stabilizing and immobilizing any fractured or broken bones, and by supporting any injured joints such as the ankle. Tissue that surrounds the affected areas is also immobilized.

Removable leg walkers or walking braces are often used by physicians to treat injuries to the lower leg and foot. Such devices are preferred in some instances over plaster or resin casts because the devices can be removed for bathing or for access to the skin during times when the skin becomes dry or otherwise irritated, or for access during additional medical treatment.

A variety of walking braces for the leg and foot have been proposed in the past and are described in various patents such as U.S. Pat. Nos. 4,320,748, 4,693,239, 4,974,583, 5,078,128 and 5,176,623. Often, such walking braces include a relatively rigid sole, a pair of rigid struts extending upwardly from opposite sides of the sole and a relatively soft, flexible boot surrounding the foot and lower leg. The struts are located over the exterior sides of the boot, and a series of fastening straps extending around the boot and over the struts are used to tighten the boot to the leg and stabilize the lower leg in relation to the foot. In addition, one or more straps secured to the sole extend over the boot in areas adjacent the patient's foot.

Known walking braces are somewhat unsatisfactory, however, in that such devices do not sufficiently address the problem of fitting the walking brace to a variety of foot and leg sizes that might be encountered. As can be appreciated, manufacturing the walking brace in a large number of different sizes substantially increases the costs of manufacture. Also, it is relatively expensive for the physician to maintain a large inventory of walking braces of differing sizes in order to be assured that a brace of the correct size, and for either foot, is available at any given time.

The fit of the walking brace is important, as a proper fit can facilitate stabilizing and healing of the injury. A properly fitting brace is also more comfortable to wear, particularly when the patient is walking. Moreover, since many types of walking braces can be removed when desired by the patient, it is important for the walking brace to be as comfortable as possible and not unduly hinder the patient's normal activities so that cooperation from the patient can be obtained in wearing the walking brace for extended periods as may be prescribed by the physician.

There is clearly a need in the art for a walking brace that can be adapted to fit a wide range of foot and leg sizes, and yet provides proper immobilization and stabilization of the bones and surrounding tissue. Such a brace should be easy for the patient to remove or install as desired, and provide sufficient comfort for the patient so that his or her activities are not unduly limited.

SUMMARY OF THE INVENTION

One aspect of the present invention relates to an orthopedic brace that comprises a sole having a longitudinal axis and a boot made of a flexible material. The boot includes a lower portion for extending over a patient's foot and an upper portion for extending above the ankle of the patient's leg. The boot includes lateral and medial sides, and a lower edge section that extends along at least one of the lateral and medial sides. The brace also includes a pair of elongated, relatively rigid struts connected to the sole and extending upwardly along the lateral and medial sides of the boots. A connector is provided for connecting the lower edge section of the boot to the sole. The connector releasably connects the lower edge section to the sole in any one of a number of positions along a reference axis generally perpendicular to the longitudinal axis of the sole so that the width of the lower portion of the boot may be varied.

Another aspect of the present invention relates to an orthopedic brace that comprises a sole, and a pair of elongated, relatively rigid struts. The struts are connected to the sole and extend in an upwardly direction. A boot is connected to the sole and has a lower portion for extending over a patient's foot and an upper portion for extending above the ankle of the patient's leg. The boot includes lateral and medial sides, and a foam inner pad and a foam outer pad. The inner pad is secured to the outer pad, and the struts are located at least partially between the inner pad and the outer pad.

The present invention also concerns an orthopedic brace that comprises a sole and a pair of elongated, relatively rigid struts. The struts are connected to the sole and extend in an upwardly direction. A boot is connected to the sole and has a lower portion for extending over a patient's foot and an upper portion for extending above the ankle of the patient's leg. The boot includes lateral, posterior and medial sides integrally connected to one another. The boot includes a lowermost terminal edge section extending along the lateral side and a lowermost terminal edge section extending along the medial side. The edge section extending along the medial side is spaced apart from the edge section that extends along the lateral side.

Another aspect of the present invention relates to an orthopedic brace that comprises a sole and a boot made of a flexible material having an outer surface. The boot includes a lower portion for extending over a patient's foot and an upper portion for extending above the ankle of the patient's leg, and the boot is connected to the sole. The brace also includes a pair of elongated, relatively rigid struts that are connected to the sole and extend upwardly along the boot. A fastening strap is provided for securing the upper portion of the boot to the patient's leg. The flexible material of the boot includes a pair of spaced apart apertures, and the strap extends through the apertures such that a section of the strap between the apertures is located inwardly of the outer surface.

The present invention additionally concerns an orthopedic walking brace comprising a sole and a boot that is connected to the sole and made of a flexible material. The boot includes a lower portion for extending over a patient's foot and an upper portion for extending above the ankle of the patient's leg. The brace also includes a pair of elongated, relatively rigid struts that are connected to the sole and extend upwardly along the boot. A first resilient insole and a second resilient insole are provided, and each has a right side and a left side. The first insole has a configuration to match a patient's right foot and has an arch support on its left side to support the plantar arch of the patient's right foot. The second insole has a configuration to match a patient's left foot and has an arch support on its right side to support the plantar arch of the patient's left foot. Each of the first insole and the second insole have a configuration for mating reception in the boot and on top of the sole, whereby either the first insole or the second insole can be selected for treatment of either a right leg or a left leg as desired.

DETAILED DESCRIPTION OF THE PREFERRED EMBODIMENTS

Figure 1:
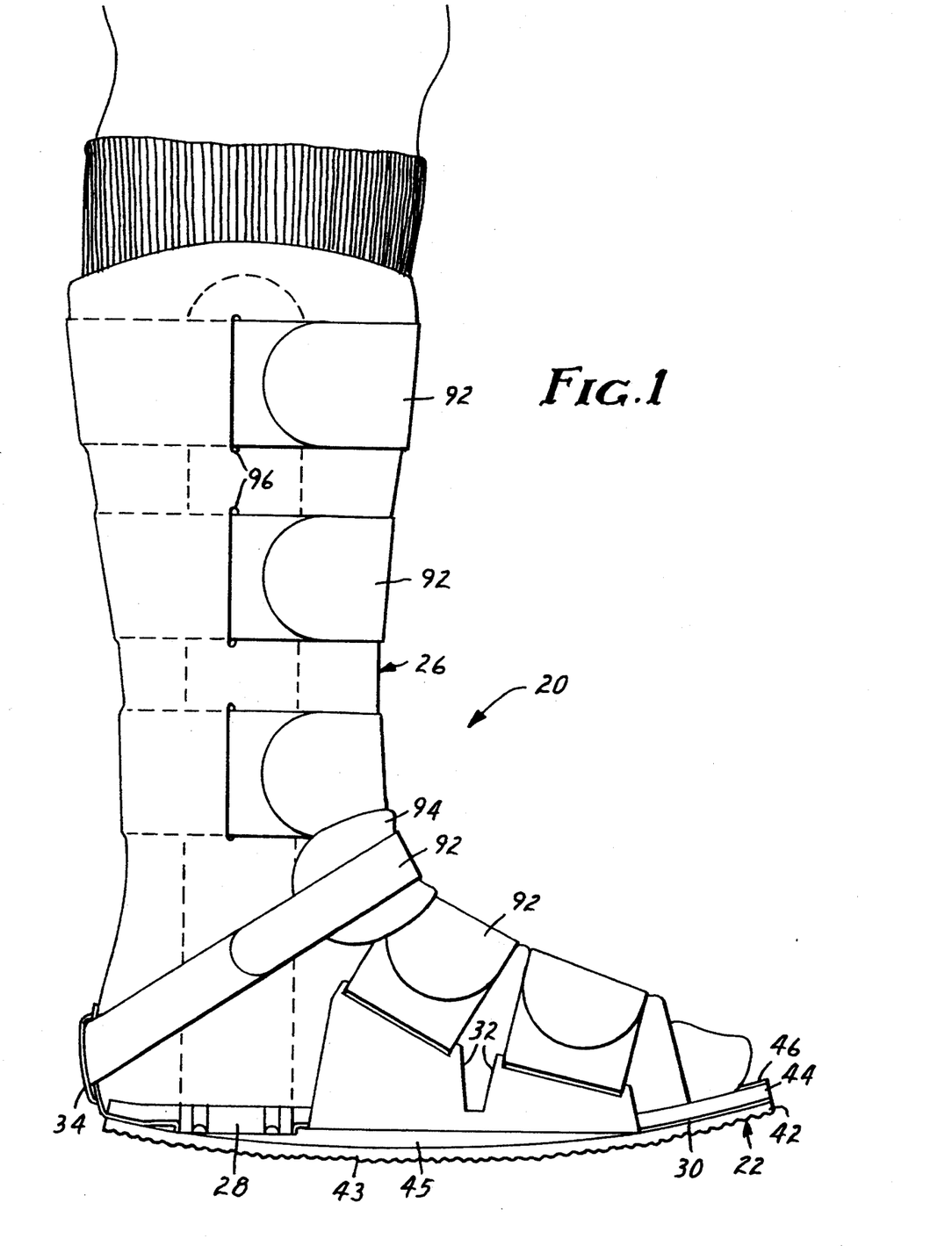
FIG. 1 is a side elevational view of an orthopedic walking brace in accordance with one embodiment of the invention.
Figure 5:
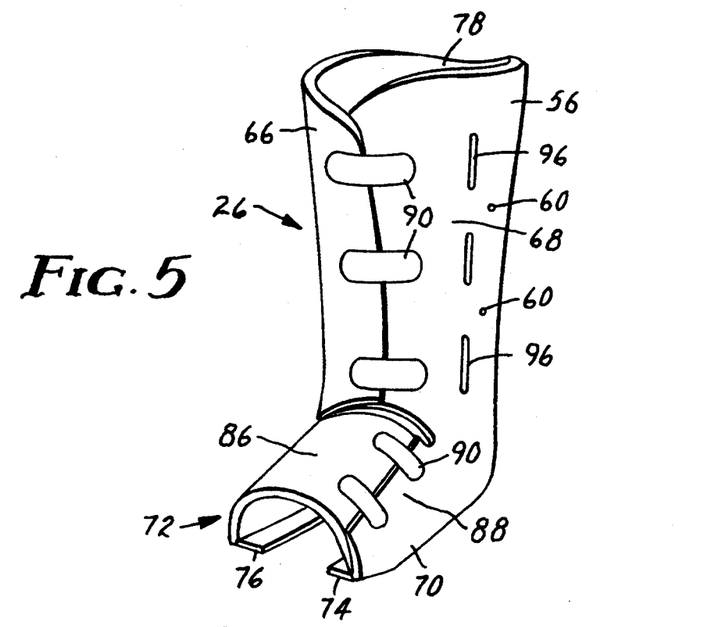
FIG. 5 is a reduced perspective view of a boot of the walking brace illustrated in FIG. 1, with fastening straps omitted for purposes of illustration.
Figure 6:
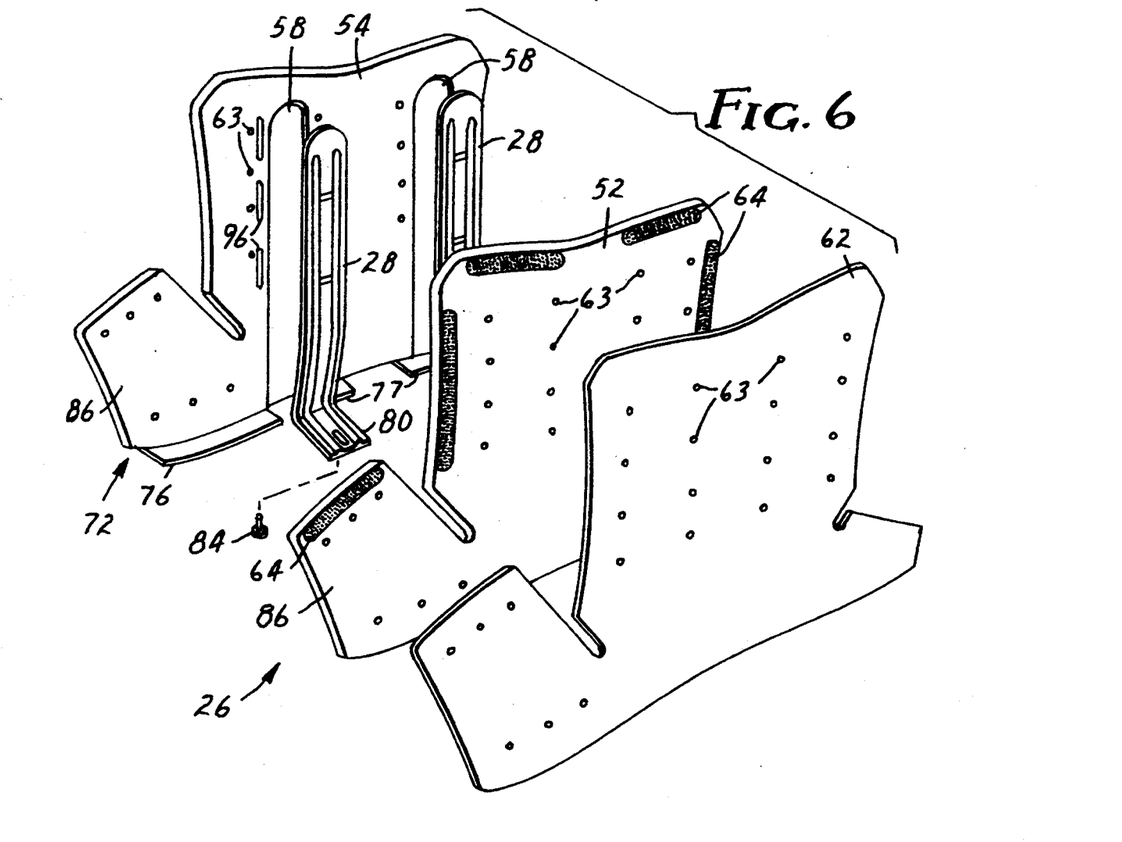
FIG. 6 is an exploded perspective view of the boot depicted in FIG. 5 along with a pair of struts except that components of the boot are shown in a flat configuration as they might appear before assembly of the boot to the sole.
Figure 7:
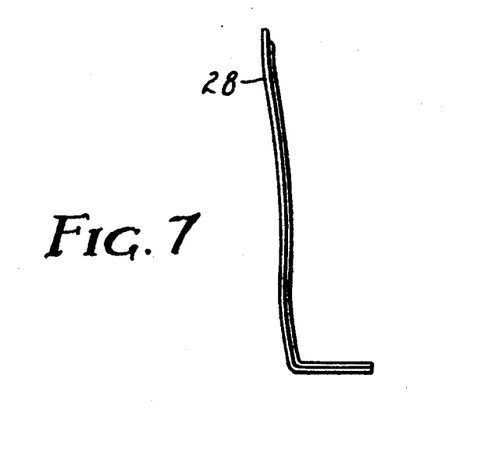
FIG. 7 is a side elevational view of one of the struts shown in FIG. 6.

An orthopedic brace according to one embodiment of the invention is illustrated in FIGS. 1-7 and is broadly designated by the numeral 20 in FIG. 1. The brace 20 includes a sole 22 (FIGS. 1 and 4), an insole 24 (FIG. 4), a boot 26 (FIGS. 1 and 5-6), and a pair of upright struts 28 (FIGS. 1 and 614 7). Although a "short leg" walking brace is illustrated, it should be understood that the invention is also useful for other orthopedic devices such as full leg walking braces and ankle braces.

Figure 2:
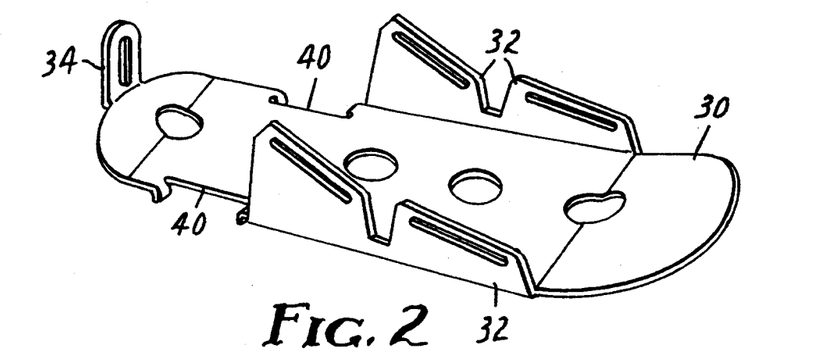
FIG. 2 is a perspective view of a rigid insert that is part of a sole of the walking brace shown in FIG. 1.
Figure 3:
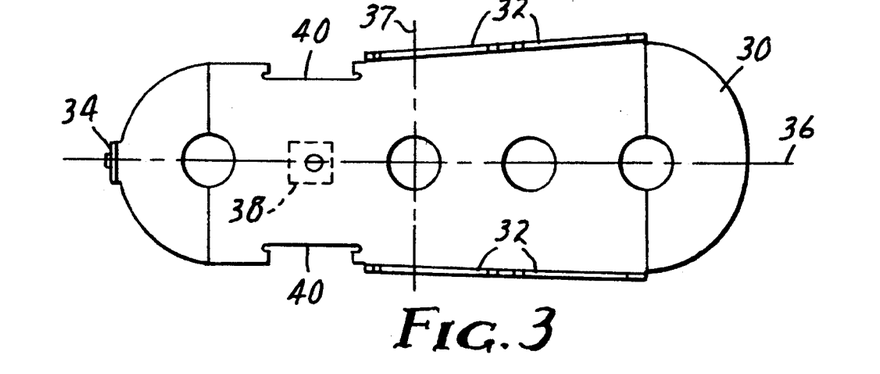
FIG. 3 is a plan view of the insert shown in FIG. 2.

The sole 22 includes an insert 30 that is shown in more detail in FIGS. 2 and 3. The insert 30 is made of a relatively rigid plastic or metallic material, such as 0.060 in. (1.5 mm) thick tempered aluminum or "aircraft" aluminum. The insert 30 includes two opposed pairs of upstanding lugs 32 located along longitudinal sides of the insert 30, as well as a single central upstanding lug 34 located at the rear of the insert 30. Each of the lugs 32, 34 includes an elongated opening.

Four holes extend through the insert 30 and are positioned along a central longitudinal reference axis 36 that is shown in FIG. 3. A threaded square nut 38 (shown by the dashed lines in FIG. 3) is welded to the bottom of the insert 30 and is also located along the longitudinal reference axis 36. As an option, use of the nut 38 may be avoided by extruding a small portion of the insert material in a downwardly direction to form a hole surrounded by thickened walls 30 and then tapping a set of threads inside the formed walls.

Two notches 40 are located along opposite longitudinal sides of the insert 30 in alignment with the nut 38. Each of the notches 40 has a front and rear side that is defined by downturned ears formed in the insert 30.

A central portion of the insert 30 is flat. A front portion of the insert 30 in front of the forward pair of lugs 32 is slightly inclined in an upwardly direction relative to the central portion of the insert 30 and is also flat or optionally curved. Likewise, a rear portion of the insert 30 behind the nut 38 and notches 40 is also inclined in a slight upward direction relative to the central portion of the insert 30 and is flat or curved. As another alternative, the entire insert 30 with the exception of the lugs 32, 34 is flat and lies in a common plane.

The sole 22 is made by adhesively bonding a bottom cushioning layer 42 and a top cushioning layer 44 to the bottom and top respectively of the insert 30. Optionally, the layers 42, 44 are also bonded to each other in areas inside the four holes of the insert 30. As another option, the layers 42, 44 extend past the periphery of the insert 30 and are integrally molded together or bonded together (e.g., by heat) in such areas such that the insert 30 is fully encased in the layers 42, 44 except for the protruding lugs 32, 34. Advantageously, provision of the four holes in the insert 30 serves to reduce the weight of the finished sole 22.

The bottom layer 42 is relatively strong and abrasion resistant in order to avoid damage from the ground or objects on the ground when the brace 20 is used for walking. The bottom layer 42, however, is somewhat resilient in order to function as a shock absorber. Preferred materials include a two-section laminate having a lower, abrasion and skid resistant section 43 made of EVA (ethyl vinyl acetate) and an upper cushioning section 45 made of a foam material such as polyethylene.

Figure 4:
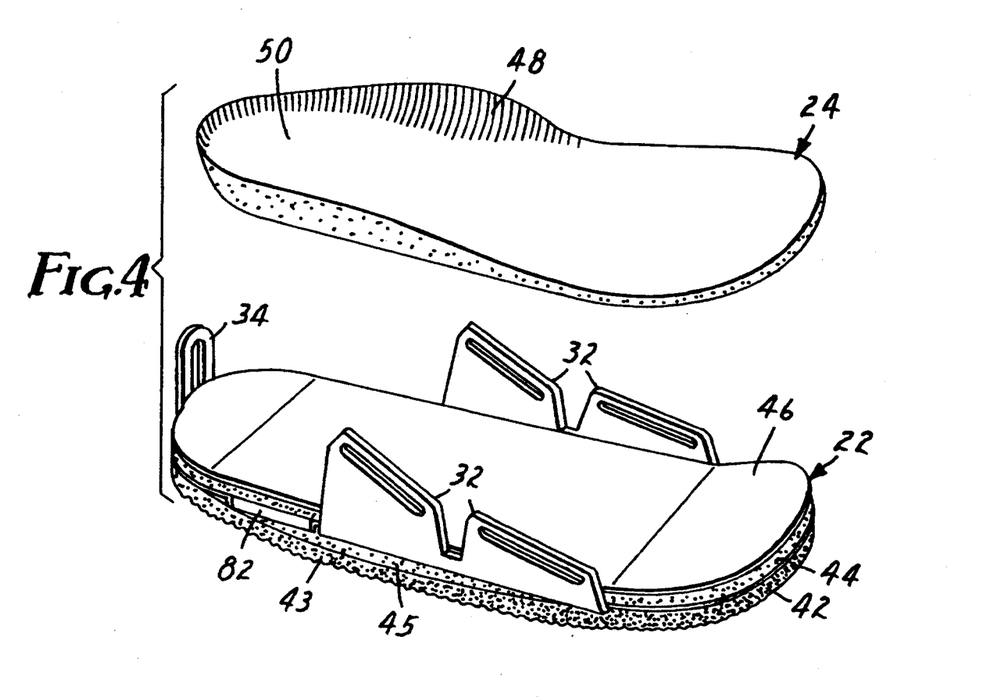
FIG. 4 is an exploded perspective view of a sole and an insole of the walking brace shown in FIG. 1.

Depending upon the selected configuration of the insert 30, the bottom layer 42 may be of uniform thickness (e.g., about 0.25 inch or 6 mm), or may vary in thickness to present a curve in directions along the longitudinal axis 36 of the sole 22. The upper section 45 of the bottom layer 42 may extend over the entire extent of the lower section 43, or, as shown in FIGS. 1 and 4, may extend only over a central portion of the sole 22. It is desirable to avoid unnecessary thickness in the sole 22 to facilitate walking by the patient, and yet provide adequate cushioning for the patient's leg.

The top layer 44 is somewhat softer and more resilient than the bottom layer 42 in order to provide additional cushioning for the patient and also to readily conform to the shape of the patient's foot. Preferred materials include foam materials such as polyethylene having a thickness of less than 0.1 in. (2.5 mm).

A loop section 46 of a hook and loop fastener extends across the entire upper surface of the top foam layer 44. It should also be noted that the sole 22 is adapted for use with either the left or right foot, as the configuration of the sole 22 is a mirror image on either side of the central reference axis 36 that is illustrated in FIG. 3.

The insole 24 that is shown in FIG. 4 is made of a molded closed cell foam material such as conformable, high density cellular urethane foam (E-A-R Specialty Composites, Cabot Safety Corporation) or an EVA material. The insole 24 is optional but preferred.

The insole 24 that is depicted in FIG. 4 is made of an EVA material and has along its left side an upstanding, gently rounded protrusion 48. The protrusion 48 is adapted to be matingly received in the patient's instep or plantar arch of the right foot. The insole 24 also includes a depressed area 50 for receiving the patient's heel.

Although not shown, another insole can also be provided in instances where the brace 20 is to be used with the left foot of the patient. In such instances, the insole will be similar to the insole 24, although the upstanding instep protrusion would be located along an opposite side, or the right side, of the insole. Consequently, the brace 20 can be readily adapted for use on either the left or right leg of the patient as desired, and the costs of maintaining and inventory for use of braces with either foot can be greatly reduced.

The boot 26 is made of a fabric and foam pad assembly as can be understood by reference to FIG. 6. The boot 26 includes an inner foam pad 52 and an outer foam pad 54, both of which are preferably made of medium density closed cell foam material such as cross-linked polyethylene having a density of 2 lb/ft$^3$ (55 gm/cm$^3$) and a thickness of about 0.25 inch (6 mm). The outer foam pad 54 is covered with an abrasion-resistant polyester fabric 56 (FIG. 5) that is bonded to the outwardly facing surface of the outer facing foam pad 54.

As shown in FIG. 6, the inner surface of the outer foam pad 54 has a pair of elongated recesses 58 to receive the upstanding leg of the struts 28. As an option, the struts 28 are retained in the recesses 58 by plastic or metal rivets 60 (FIG. 5) that extend through the outer fabric 56, the outer foam pad 54 and elongated horizontal slots in the struts 28. The width of the recesses 58 is greater than the width of the struts 28. The slots in the struts 28 enable the struts 28 to move as needed in the recesses 58 in a lateral direction (i.e., toward the front or rear of the boot 26) when the boot 26 is closed around the leg of a patient, so that the boot 26 is adaptable to fit various legs with differing circumferential dimensions.

The inner foam pad 52 is bonded to the outer foam pad 54 by heat or by a suitable adhesive. Advantageously, the upright leg of the struts 28 is encased between the pads 52, 54 and thus does not engage the patient's skin, and is not present on the outside of the boot 26 where it might otherwise present a hazard by snagging with another object, or by unexpectedly engaging the patient or another person.

The boot 26 also includes an inner layer of soft fabric 62 for contact with the patient's skin. Preferably, the fabric 62 is made of a washable, breathable fabric such as cotton or a microporous thermoplastic film (such as is sold under the trademarks GORTEX and COOLMAX) that facilitates wicking of perspiration away from the patient's skin. Also, as illustrated in FIG. 6, the boot 26 is provided with a series of holes 63 (shown only in FIG. 6) that extend through the pads 52, 54 and the layers of fabric 56, 62 in aligned relation to enhance ventilation to areas interiorly of the boot 26.

The inner layer of fabric 62 is releasably connected to the inner foam pad 52 by elongated, spaced apart segments 64 of a hook and loop fastener. One section (i.e., either the hook section or the loop section) of the hook and loop fastener assembly is fixed to the inner foam pad 52, while the other section (not shown) of the hook and loop fastener assembly is secured to the side of the inner layer of fabric 62 that faces the foam pad 52. In this manner, the inner layer of fabric 62 can be detached from remaining components of the boot 26 by the patient and laundered when desired.

The boot 26 has two opposite sides that, when worn on the right leg of the patient, may be termed a lateral side 66 and a medial side 68 (FIG. 5). Such terms, however, are used only for exemplary purposes, as the boot 26 is adapted to be worn on either leg and does not have a configuration that would restrict use of the boot 26 to one leg or the other. The boot 26 also has a posterior side 78. A free, terminal lowermost bottom edge section 70 extends along the bottom of the lateral side 66, the medial side 68 and the posterior side 78.

A connector 72 for connecting the lowermost edge section 70 of the boot 26 to the sole 22 includes an elongated medial flange piece 74 that is secured to the lowermost edge section of the medial side 68, an elongated lateral flange piece 76 that is secured to the lowermost edge section 70 of the lateral side 66 and two posterior flange pieces 77 (or optionally a single, central posterior flange piece) that are secured to the lowermost edge section 70 of the posterior side 78. Preferably, each of the flange pieces 74,76,77 is integrally connected to the outer foam pad 54 (see FIG. 6) and is separated from the outer pad 54 by a hinge-type crimp made by applying heat and pressure to the foam material, so that the pieces 74,76,77 can be easily pivoted inwardly relative to the pad 54. The connector 72 includes a hook and loop fastener having a hook section and a loop section, wherein the medial piece 74 and the lateral piece 76 include one of the hook section and the loop section and wherein the other of the hook section and the loop section is fixedly connected to the sole 22. In the embodiment shown in the drawings, each piece 74, 76, 77 carries on its lower side a hook section of a hook and loop fastener of the connector 72, and the connector 72 also includes the loop section 46 mentioned earlier.

When the brace 20 is assembled, the flange pieces 74,76,77 are folded inwardly toward the interior of the boot 26 and laid atop the sole 22, such that the hook section of each flange piece 74,76,77 flatly contacts the loop section 46 lying atop the top foam layer 44 of the sole 22. Inasmuch as the hook and loop fastener sections are releasable, the flange pieces 74, 76 may each be connected to the sole 22 in any one of a number of positions along a reference axis 37 generally perpendicular to the reference axis 36 shown in FIG. 3, so that the distance between the lowermost edge section 70 of the lateral side 66 and the medial side 68 may be varied. In this manner, the width of the lower portion of the boot 26 can be adjusted as needed to conform to the width of the patient's foot. The flange pieces 77 may also be detached from the loop section 46 and repositioned as needed.

In assembling the boot 26 to the sole 22, the lateral side 66 and the medial side 68 are each bent in a curve around the posterior side 78 of the boot 26. The lowermost edge section 70 of the lateral and medial sides 66, 68 are spaced apart from each other, but are held in position by the connector 72 that secures the edge sections 70 to the sole 22. Such construction differs from certain traditional boots for walking braces that are made by extending lateral and medial sides upwardly from a bottom portion, and then stitching the sides together along a seam located at the posterior side of the boot. In accordance with the present invention, no stitching or otherwise seaming rear edges of the boot is necessary. Optionally, to facilitate assembly of the boot 26, the foam pads 52, 54 are shaped under heat and pressure to retain a configuration approximating the configuration shown in FIG. 5.

Once the flange pieces 74,76,77 are placed on top of the sole 22, the insole 24 is inserted in the boot 26 and placed over the flange pieces 74,76,77, as well as the portion of the sole 22 that is exposed between the facing edges of the flange pieces 74, 76. The insole 24 is preferably of a width that matches the width of the patient's foot, and covers substantially all of the loop fastener section 46 that is on top of the sole 22 within the confines of the boot 26. The periphery of the insole 24 is cut as needed in order to have a shape that is complemental in shape to the adjacent inner peripheral regions of the boot 26. Advantageously, when the brace 20 is worn, the portion of the patient's weight that is carried by the leg in the brace 20 causes the corresponding foot to bear down on the insole 24 and retain the hook section of the underlying flange pieces 74,76,77 in locked engagement with the loop section 46, so that the boot 26 remains firmly connected to the sole 22.

Each of the struts 28 has a generally "L"-shaped configuration when viewed from its sides as illustrated in FIG. 7. The lower, horizontal leg of each strut 28 includes an elongated slot 80 that is shown in FIG. 6. As the boot 26 is assembled to the sole 22, the horizontal legs of the struts 28 are guided into a channel 82 (FIG. 4). The channel 82 is formed in the foam section 45 of the sole 22 and extends between the notches 40 of the insert 30.

The horizontal legs of the struts 28 overlap each other when inserted into the channel 82 and a coupling, such as a small bolt 84 (FIG. 6), is guided through a small opening in the bottom layer 42 of the sole 22. The bolt 84 is inserted into the overlapping slots 80 and threaded into the nut 38 in order to releasably lock the struts 28 to the sole 22. Preferably, the struts 28 have a pair of spaced apart strengthening ribs, and the nut 38 is complementally received in the space between the ribs of the horizontal leg of one strut 28. The horizontal leg of the other strut 28 nests with the ribs of the overlying leg, and the nut 38 together with the nesting ribs helps resist pivotal movement of the struts 28 about a vertical axis.

The bolt 84, in combination with the slots 80, enable each strut 28 to be connected to the sole 22 in any one of a number of positions along a reference axis generally perpendicular to the longitudinal reference axis 36 (FIG. 3) of the sole 22 so that the distance between the struts 28 may be varied. In practice, when assembling the brace 20, the hook and loop fastener of the connector 72 is used to adjust the distance between the sides 66, 68 of the boot 26, and then the bolt 84 is tightened to releasably fix the struts 28 at a proper distance apart from each other once the boot 26 is placed on the patient, so that the width of the boot 26 in areas adjacent the patient's foot is closely complemental to the configuration of the foot. Adjustments in the width of the boot 26 can be readily made when the bolt 84 is loosened and the patient's foot is removed, by simply removing the insole 24 and disengaging the flange pieces 74, 76 from the loop section 46 and replacing the pieces 74, 76 at appropriate locations as desired.

The boot 26 has a front opening for entry and exit of the patient's leg. An upper portion of the opening is centrally located along the front of the boot 26 and is defined by front terminal edges of the lateral and medial sides 66, 68. The lower portion of the front opening, corresponding to areas over the patient's foot, is located laterally in a horizontal direction from the upper portion of the opening as can be observed in FIG. 5. The lower portion of the opening is located laterally of a vertical reference plane that is centrally located between the lateral and medial sides 66, 68.

As illustrated in FIG. 6, the pads 52, 54 (as well as the fabric layers 56, 62) have a lateral flap 86 that is substantially longer (in directions from the lowermost edge sections 70) than a medial flap 88 that is located on an opposite side of the boot 26. Preferably, the lateral flap 86 is of a length sufficient to extend over the lateral side of the foot, to extend over the entire top of the foot across its width, and optionally to extend over a portion of the medial side of the patient's foot and adjacent the lowermost edge section 70 of the medial side as depicted in FIG. 5. In instances where the patient has suffered a metatarsal fracture, the elongated lateral flap 86 is an advantage because there is no flap edge that is located along the top of the foot and might otherwise cause discomfort.

Once the patient's foot and leg are in the boot 26, a series of relatively short strap fasteners 90 (FIG. 5) are utilized to close the front opening of the boot 26. Each of the strap fasteners 90 includes an elongated section of fabric that is fixed on one end to the lateral side 66 of the boot 26, and carries on its free end either a hook section or a loop section of a hook and loop fastening assembly. The remaining section of the hook and loop fastening assembly is connected along the medial side 68 of the boot 26.

Next, longer, outer fastening straps 92 (shown in FIG. 1, and omitted in FIGS. 5–6) are used to more tightly secure the boot 26 and the sole 22 to the patient's leg. Two lower straps 92 are secured to the lugs 32 of the sole 22. Three upper straps 92 encircle the patient's lower leg above the ankle in areas adjacent the upper portion of the boot 26. A sixth outer strap 92, narrower in width than the other five straps 92, extends through the lug 34 of the insert 30, and carries a short section of padding 94.

The outer fastening straps 92 each include end sections with a hook and loop fastening assembly, so that the boot 26 may be tightly secured to the patient's foot and leg. Preferably, at least the sixth strap 92 (that extends through lug 34), and optionally all of the straps 92, include a loop section of the hook and loop assembly that is mounted on a stretchable substrate, such as "VELSTRETCH" brand loop component (Velcro USA).

The three upper straps 92 each include a section that extends through apertures 96 (FIGS. 1 and 5–6) located in the lateral side 66 and the medial side 68 of the outer foam pad 54. Therefore, an intermediate section (shown in dashed lines in FIG. 1) of each of the three upper outer straps 92 that is between the apertures 96 is located inwardly of the outer foam pad 54 and extends through interior portions of the boot 26 between the foam pads 52, 54 while the aforementioned end sections (shown in full lines in FIG. 1) of the same straps are located outwardly of the outer surface of the foam pad 54. Such construction is an advantage in that the aforementioned sections of the straps 92 are hidden from view and cannot normally become entangled or snag with other items.

As another option, the fabric 56 is replaced in its entirety with a substrate that carries a loop section of a hook and loop fastening assembly. With this option, the three upper straps 92 have an additional hook section that may be releasably coupled to any one of a number of varying locations on the boot 26, so that an optimal location and orientation for such straps 92 can be achieved. Additionally, the strap fasteners 90 as described above are replaced with this option by flexible strips having along their entire length a hook section that can then be releasably coupled to the substrate on both sides of the front opening.

Figure 8:
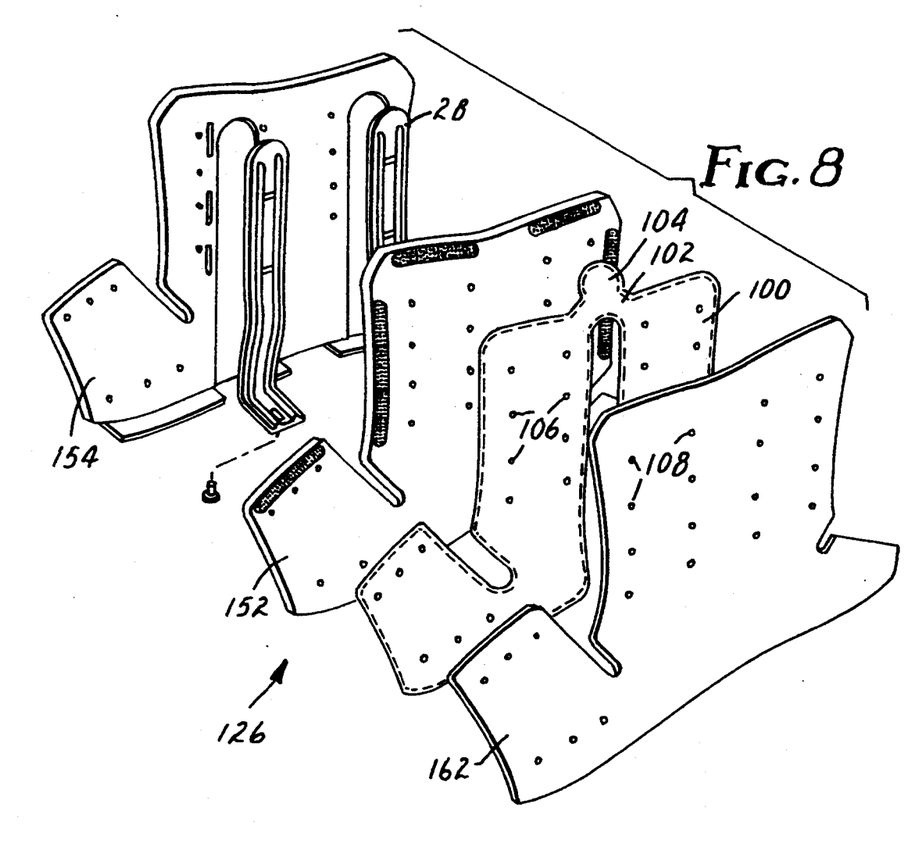
FIG. 8 is an exploded perspective view of a boot and a pair of struts of a walking brace constructed in accordance with another embodiment of the invention, wherein components of the boot are shown in a flat configuration.

In an alternate embodiment of the invention, boot 126 includes an inner foam pad 152, an outer foam pad 154, an outer fabric (not shown) and an inner layer of fabric 162 that are substantially all identical to the inner foam pad 52, the outer foam pad 54, the outer layer of fabric 56 and the inner layer of fabric 62 and thus will not be described again in detail. Other elements of the brace according to this embodiment, other than the boot 126, are also substantially identical to the corresponding elements mentioned in connection with the brace 20, and no additional description is necessary in this regard. However, boot 126 includes a pair of inflatable air bladders 100 that are connected by channels 102 to a common single bulb-type pump 104. Preferably, the bladders 100 are located along the dorsal side of a patient's calf. Each bladder 100 is connected to bulb pump 104 by separate one-way check valves disposed in channels 102. Each bladder 100 also preferably incorporates an outlet valve for releasing pressure individually from each bladder. In that way, pressure in each individual bladder 100 can be separately controlled for a patient's comfort. The outlet valves are preferably spring-loaded ball and socket types which are depressed to allow air or other pressurized gas to escape from the bladder 100. The bladders 100, the channels 102 and the pump 104 are described in detail in copending U.S. patent application Ser. No. 08/121,733 filed Sep. 15, 1993.

The bladders 100 are preferably constructed of plastic materials, most preferably thermoplastic to allow the use of conventional heat sealing to form the bladders. Examples of thermoplastic materials which can be used to form bladders according to the present invention include, but are not limited to: polyurethane, ethylene vinyl acetate copolymers, polyethylene, polypropylene, polyvinyl chloride, polyesters, poly(styrene/butadiene), poly(styrene/butadiene/isoprene), etc. Natural or synthetic rubbers can also be used with the appropriate bonding system to form bladders according to the present invention. Furthermore, blends and/or laminates of thermoplastics can be used to form the bladders.

Upper and lower sheets of each bladder 100 are preferably bonded together in the interior of each bladder 100 and spaced throughout each bladder 100. Within each bonded area is a through-hole 106 which allows ventilation through bladders 10. Optionally, the bladder may contain an open cell foam material (preferably urethane) or a resilient nonwoven fabric. The through-holes 106 are aligned with holes 108 that extend through the pads 152, 154, the inner layer of fabric 162 and the outer layer of fabric. As a result, ventilation is provided to underlying areas of the patient's skin. The bonded areas and corresponding holes 106 could be dispersed in any pattern throughout the area covered by bladders 100. It will also be understood that the bonded areas and holes 106 could take many shapes and should not be limited to the rounded shapes depicted in FIG. 8. Examples of other shapes include, but are not limited to, ovals, ellipses, rectangles, squares, polygons, etc.

The spacing and size of the bonded areas provide bladders 100 with a baffle design which helps to disperse the air or other pressurized gas contained within bladders 100. Furthermore, each bonded area forms a recess in the bladder 100 which limits the bladder's area of contact with a patient's skin because the material in and near to the bonded areas is raised from contact with the skin. The recessed areas also allow perspiration which accumulates underneath the bladders 100 to evaporate through holes 106 in the bonded areas. The bonded areas could also be connected to each other to further enhance the baffling function of the bonded areas.

The pump 104 includes an upper bulb cover having an inlet port. Located within the pump 104 is a porous compressible material such as open cell foam which provides resiliency to the bulb during the pumping process. When compressed with the inlet port sealed, the bulb pump forces air through the one-way valves located in channels 102. The air then enters bladders 100 and pressurizes them to the desired level.

The overall combined configuration of the bladders 100 is slightly smaller than the peripheral configuration of the inner foam pad 152 and the inner layer of fabric 162, so that a peripheral edge section of the inner foam pad 152 and the inner layer of fabric 162 is available for attachment of sections of a hook and loop fastening assembly that releasably connects the inner layer of fabric 162 to the remaining components of the boot 26. The bladders 100 are bonded to the inner foam pad 152 by an adhesive or by a flame lamination or heat staking process.

Advantageously, after the pump 104 is used to inflate the bladders 100, the channels 102 may be folded over themselves to enable the pump 104 to be pivoted downwardly and tucked inside the upper portion of the posterior side of the boot 126 in an out-of-the-way location. As an option, a pocket inside the upper portion of the posterior side may be provided between the pads 152, 154 to receive the pump 104.

We claim:

1. An orthopedic brace comprising:
   a sole having a longitudinal axis;
   a boot made of a flexible material, said boot including a lower portion for extending over a patient's foot and an upper portion for extending above the ankle of the patient's leg, said boot including lateral and medial sides, said boot including a free, terminal bottom edge section extending along and below at least one of said lateral and medial sides;
   a pair of elongated, relatively rigid struts connected to said sole and extending upwardly along said lateral and medial sides of the boot; and
   a connector for connecting said free, terminal bottom edge section of said boot to said sole, said connector releasably connecting said free, terminal bottom edge section to said sole in any one of a number of positions along a reference axis generally perpendicular to said longitudinal axis of said sole so that the width of said lower portion of said boot may be varied.

2. The orthopedic brace of claim 1; including a coupling for adjustably connecting at least one of said struts directly to said sole in any one of a number of positions along a reference axis generally perpendicular to said longitudinal axis of said sole so that the distance between said struts may be varied.

3. The orthopedic brace of claim 1, wherein said connector includes an elongated flange piece extending along said bottom edge section and flatly lying on said sole and wherein said orthopedic brace further includes an insole extending over said elongated piece of said connector.

4. The orthopedic brace of claim 3, wherein said connector includes a hook and loop fastener having a hook section and a loop section, wherein said elongated piece includes said hook section, and wherein said sole has an upper surface, and wherein said loop section extends over and is connected to said upper surface of said sole.

5. The orthopedic brace of claim 4, wherein said loop section extends substantially over the entire extent of said upper surface.

6. The orthopedic brace of claim 1, wherein said bottom edge section of said boot extends along both of said lateral and medial sides, wherein said connector includes an elongated medial piece extending along said bottom edge section beneath said medial side and an elongated lateral piece extending along said bottom edge section beneath said lateral side, wherein said medial piece and said lateral piece lie on said sole, and wherein said orthopedic brace further includes an insole extending over said medial piece and said lateral piece.

7. The orthopedic brace of claim 6, wherein said medial piece is not directly connected to said lateral piece.

8. The orthopedic brace of claim 6, wherein said connector includes a hook and loop fastener having a hook section and a loop section, wherein said medial piece and said lateral piece include one of said hook section and said loop section and wherein the other of said hook section and said loop section is fixedly connected to said sole.

9. The orthopedic brace of claim 1, wherein said boot includes a foam inner pad and a foam outer pad, and wherein said struts are directly connected to said sole and are located at least partially between said inner pad and said outer pad.

10. The orthopedic brace of claim 1, wherein said boot has a front opening for entry and exit of the patient's leg, wherein said opening includes an upper portion to extend along the patient's leg above the ankle and a lower portion to extend over a portion of the patient's foot, said lower portion of said opening being located laterally of a reference plane centrally located between said lateral side and said medial side.

11. An orthopedic brace comprising:
a sole;
a boot made of a flexible material having an outer surface, said boot including a lower portion for extending over a patient's foot and an upper portion for extending above the ankle of the patient's leg, said boot being connected to said sole, at least said upper portion including an inner resilient pad and an outer resilient pad;
a pair of elongated, relatively rigid struts connected to said sole and extending upwardly along said boot; and
a plurality of fastening straps located on said upper portion of said boot for securing said upper portion of said boot to the patient's leg, said upper portion of said boot including a plurality of pairs of spaced apart apertures, each of said straps including two end sections and an intermediate section, each of said straps extending through a respective pair of said apertures such that said intermediate section of each strap is between said respective pair of apertures and is located inwardly of said outer surface and between said inner pad and said outer pad and said end sections of each strap are located outwardly of said outer surface.

12. The orthopedic brace of claim 11, wherein said apertures are located in said outer pad.

13. The orthopedic brace of claim 11 wherein said inner pad and said outer pad are made of a foam material.

14. The orthopedic brace of claim 11 wherein said pair of struts are located between said inner pad and said outer pad.

* * * * *